United States Patent [19]

Thonar

[11] Patent Number: 4,704,356
[45] Date of Patent: Nov. 3, 1987

[54] METHOD OF DIAGNOSING CARTILAGE TISSUE ABNORMALITIES

[75] Inventor: Eugene J. Thonar, Berwyn, Ill.

[73] Assignee: Rush-Presbyterian-St. Luke's Medical Center, Chicago, Ill.

[21] Appl. No.: 594,112

[22] Filed: Mar. 27, 1984

[51] Int. Cl.[4] .................. G01N 33/53; G01N 33/577
[52] U.S. Cl. ...................................... 435/7; 436/501; 436/548; 436/811; 436/815; 935/110
[58] Field of Search ................ 435/7; 436/501, 548, 436/811, 815; 935/110

[56] References Cited

PUBLICATIONS

Caterson et al, J. Biol. Chem., 258(1983), 8848–54.
Conrad et al, J. Biol. Chem., 257(1982), 464–71.
Calatroni et al, J. Clin. Inves., 48(1969), 332–43.
Yutaka et al, Clin. Chim. Acta, 125(1982), 233–40.
Roughley et al, J. Biol. Chem., 256(1981), 12699–12704.
Wu et al, Analyt. Biochem., 139(1984), 218–23.
Yutaka et al, Clin. Chim. Acta, 122(1982), 169–80.
A. L. Fluharty, *The Journal of Investigative Dermatology,* 79: 38s–44s (1982).
E. J-M. Thonar et al., *The Journal of Biochemistry,* 257: 14173–14180 (1982).

*Primary Examiner*—Christine M. Nucker
*Attorney, Agent, or Firm*—Fitch, Even, Tabin & Flannery

[57] ABSTRACT

It is found that abnormal levels of keratan sulfate in the peripheral blood are indicative of abnormalities of cartilage or cartilage-like tissues. Specifically, elevated levels of keratan sulfate in the peripheral blood plasma or serum are indicative of osteoarthritis and either substantially complete absence of or very elevated levels of keratan sulfate in the peripheral blood are indicative of muscular dystrophy and related disorders. The level of keratan sulfate in the peripheral blood is determined by an immunoassay using a monoclonal antibody. Preferably the immunoassay employs a colorimetric reporter system.

6 Claims, No Drawings

METHOD OF DIAGNOSING CARTILAGE TISSUE ABNORMALITIES

The present invention relates to a method of detecting disorders affecting cartilage or related tissues and more particularly to a method of detecting such disorders by measuring the concentration of keratan sulfate in peripheral blood.

BACKGROUND OF THE INVENTION

A large number of individuals are afflicted with disorders of cartilage or cartilage-like tissues, and hence, the makeup of normal and abnormal cartilage tissue as well as the breakdown of cartilage tissue is an important topic of current investigations. Osteoarthritis is a condition characterized by the breakdown of cartilage tissue and occurs in the majority of individuals over the age of 55. One of the most important causes of absenteeism from the workplace is chronic back pain, which in many cases is related to deterioration of the discs which are between the vertebrae and which are formed of tissue that is closely related to cartilage. Another tissue that is related to cartilage is the tissue that comprises the cornea of the eye, and there are indications that the cornea-clouding, blindness-causing disease, macular dystrophy, results from the inability of certain individuals to biosynthesize the macromolecules present in normal corneal tissue.

Diagnosis of cartilage, disc, or corneal disorders is often only detected after the disorders have reached relatively advanced stages where the individual experiences pain in the joints or the back, or, in the case of macular dystrophy, is beginning to lose his sight. It would be desirable to have a method of diagnosing the onset of cartilage, disc or corneal tissue disorders before they become symptomatic.

Proteoglycans are major components of the extracellular matrix of cartilage where they are found largely organized into aggregates. These aggregates contain proteoglycan molecules which can specifically bind to hyaluronic acid through a portion of the molecule termed the hyaluronic acid-binding region.

A cartilage tissue proteoglycan molecule has a core protein backbone of approximately 2000-4000 amino acid residues. One end of this core protein contains N-linked oligosaccharides and is able to interact very specifically with hyaluronic acid. It is termed the hyaluronic acid-binding region. The major portion of the protein moiety is rich in covalently attached glycosaminoglycan moieties, particularly keratan sulfate and chondroitin sulfate. Keratan sulfate moieties are found both in a keratan sulfate-rich region which is poor in chondroitin sulfate and in the major polysaccharide attachment region where one finds the majority of the chondroitin sulfate chains. Chondroitin sulfate moieties have molecular weights ranging in humans from approximately 5000 in disc tissue to approximately 15,000 to 20,000 in young articular cartilage. Keratan sulfate ranges in molecular weight from approximately 3000 to approximately 9000, being slightly larger in disc tissue than in articular cartilage. Keratan sulfate consists of a repeating sequence of the disaccharide, glucosamine-galactose. The degree to which each of these two sugars is sulfated varies with the source of the keratan sulfate. It is as yet unclear what the exact composition of the sequence of sugars which make up the linkage region linking the keratan sulfate molecules to the protein is.

During postnatal life, proteoglycan molecules change with respect to size and chemical composition. The changes include modifications in the size of the chondroitin sulfate chains as well as in the relative content of chondroitin sulfate, keratan sulfate, and oligosaccharide molecules covalently attached to the core protein. The glycosaminoglycan moieties, particularly keratan sulfate, have thus been the object of recent studies. For example, it has been shown that proteoglycans isolated from osteoarthritic cartilage have compositions that are similar to those of proteoglycans isolated from immature tissue. Chondrocytes (cartilage cells), in an attempt at tissue repair, apparently switch to the biosynthesis of immature proteoglycans that are poor in keratan sulfate. Keratan sulfate content has been found to relate to cartilage stiffness, and it has been suggested that low keratan sulfate proteoglycans are unsuitable for the load-bearing requirements of joints.

Despite the fact that keratan sulfate has been the subject of recent investigation as relates to cartilage tissue, relatively little is known about keratan sulfate. Not only has keratan sulfate not yet been fully characterized, but little is known about its breakdown, or more generally about its metabolism.

Nevertheless, it is known that keratan sulfate is quite tissue specific being naturally present only in cartilage, disc, and corneal tissue. Chondroitin sulfate, on the other hand, is not as tissue specific, being found in a variety of other connective tissues. Clearly, keratan sulfate is a more specific indicator of cartilage group tissue, its precursors and its breakdown products than is chondroitin sulfate.

SUMMARY OF THE INVENTION

It is found that whereas keratan sulfate is ordinarily found in low level in the peripheral blood of patients having abnormalities of cartilage, disc, or corneal tissues, keratan sulfate may be present in abnormally high or abnormally low levels. A quantitative immunoassay for keratan sulfate in the peripheral blood has been developed. Correlations between abnormal levels of keratan sulfate in the peripheral blood and disorders of cartilage, disc, or corneal tissue have been found to exist. Abnormally low levels and abnormally high levels of keratan sulfate in peripheral blood have been correlated with macular dystrophy, a corneal disorder that generally leads to blindness, as well as with related corneal disorders. Patients with osteoarthritis tend to have abnormally high levels of keratan sulfate.

DETAILED DESCRIPTION OF THE PREFERRED EMBODIMENTS

In accordance with the present invention, it is found that the level of keratan sulfate in the peripheral blood is an important indicator of disorders of cartilage, disc, and corneal tissues. Hereinafter, these keratan sulfate-containing tissues will be referred to generically as cartilage-group tissues. In particular, abnormally low levels and abnormally high levels of keratan sulfate in the peripheral blood have been correlated with macular dystrophy and related corneal disorders. Abnormally high levels of keratan sulfate in the peripheral blood have been correlated with osteoarthritis.

In accordance with a preferred aspect of the present invention, keratan sulfate levels in peripheral blood plasma or serum are quantitated by an immunoassay which is sufficiently sensitive to differentiate between low, normal, and elevated levels of keratan sulfate in peripheral blood. In particular, an enzyme-linked immunosorbent assay has been developed that includes an inhibition step and that uses a monoclonal antibody that is specifically reactive with keratan sulfate.

That cartilage-group tissue disorders are indicated by abnormal keratan sulfate levels in the peripheral blood is surprising and unexpected because the keratan sulfate level in the peripheral blood has not been previously studied to any significant extent and has not been expected to disclose important information. Keratan sulfate level in peripheral blood as an indicator of pathologic conditions has not been previously considered because the level of keratan sulfate in peripheral blood is so low that it was considered to be effectively nondetectable. As such, keratan sulfate levels in peripheral blood have not been closely examined. Furthermore, keratan sulfate is chemically similar to components that are present in significantly higher levels in blood serum and plasma, and the prior lack of any quantitative test specific for keratan sulfate at the level it is present in blood has prevented observations being made about keratan sulfate levels in peripheral blood.

The discovery of clinically meaningful levels of keratan sulfate in the peripheral blood came about during development of an assay for keratan sulfate in cartilage tissue. Peripheral blood serum or plasma, which was believed to contain insignificant amounts of keratan sulfate, was chosen as a suitable negative control for keratan sulfate assays. Very unexpectedly, blood samples were found to indeed contain significant, albeit low, levels of keratan sulfate, leading to the inquiry of whether such significant levels of keratan sulfate in peripheral blood were indicative of cartilage-group tissue disorders, and this proved to be the case.

An immunoassay that was specifically developed for keratan sulfate level measurement is an enzyme-linked immunosorbent assay (ELISA) that is based upon a sandwich technique such as that which has been used previously to determine titers and specificity of antisera as well as to measure antigens both qualitatively and quantitatively. In the assay that has been specifically developed, the antigen (keratan sulfate) is measured quantitatively by incorporation of an antibody inhibition step. Briefly, microtiter plates are coated with a keratan sulfate-containing substance, such as bovine nasal D1 proteoglycan (BNP). (Keratan sulfate of a variety of mammalian species has a similar structure to that of human keratan sulfate and may react interchangeably with antibody reactive with human keratan sulfate; however, where nonhuman proteoglycan is used as the standard against which levels of human keratan sulfate are measured, it is appropriate to express human keratan sulfate levels as equivalents of the nonhuman proteoglycan.)

As the inhibition step, in separate vials, aliquots of a solution containing keratan sulfate-reactive antibody (preferably monoclonal antibody) is incubated with various known concentrations of a keratan sulfate-containing substance as well as with unknown specimens of blood plasma or serum for a period of time that is sufficient to permit substantially complete reaction of the antibody with keratan sulfate. Thereafter, equal amounts of the incubation mixtures are applied to the keratan sulfate-coated plates and incubated for a period of time sufficient for antibody, which was not prereacted (inhibited) with the keratan sulfate in solution, to react with the keratan sulfate that is coated on the plates. Then the plates are washed thoroughly to remove all antibody, keratan sulfate, and antibody-keratan sulfate complex that is not bound to the plate.

As a means of visualizing the amount of antibody that is bound to the plate, the plate is exposed to an excess of a second antibody that reacts with the anti-keratan sulfate antibody and which is appropriately labeled with an enzyme. For example, if the first antibody is an anti-keratan sulfate monoclonal mouse antibody, the enzyme label may be linked to anti-mouse immunoglobulin. A preferred means of labeling the second antibody is by linkage to an enzyme, such as peroxidase, which catalyzes a colorimetric reaction by which its presence is reported. An example of a suitable peroxidase catalyzed reporter reaction is described in the *Journal of Biological Chemistry* 257: 14173–14180, 1982. Other enzymatic reporter systems may be substituted for the peroxidase reporter system as a means for visualizing keratan sulfate-bound antibodies.

In this particular assay system, the more keratan sulfate that is present in the specimen, the less color that develops. Although the degree of color development is a function of keratan sulfate concentration in the specimen, it is not a linear relationship. Accordingly, it is necessary to prepare a standard curve from known keratan sulfate standard concentrations against which the color development in an unknown specimen may be compared. The standard curve for this assay is generally linear over only a limited keratan sulfate concentration range, and in order that the level of keratan sulfate in an unknown specimen may be read with accuracy from a standard curve, it is preferred to perform the assay on serial dilutions of each specimen to assure that one or more of the serial dilutions of each specimen assays fall within the linear range.

A variation on the ELISA assay described above is to bind anti-keratan sulfate antibody to the solid support. Also required in this case is enzyme linked to a molecule containing keratan sulfate. A known quantity of the enzyme-linked keratan sulfate-containing molecule is added to a known amount of test specimens and a fixed amount of such mixtures are placed in the coated wells. Keratan sulfate in the test specimens competes for antibody binding sites with the keratan sulfate in the enzyme-linked molecules. After an approximate amount of time, the wells are washed and subsequently exposed to a reagent system that undergoes an enzyme-catalyzed colorimetric reaction, with, in this case, greater color development indicating less free keratan sulfate in the reaction mixture. This assay system has the advantage of being somewhat simpler, requiring only antibody linked to a plate, an enzyme-linked keratan sulfate solution, and an enzyme substrate solution. This assay system may be more suitable for providing in kit form to a medical laboratory.

Radioimmunoassays represent another suitable technique whereby keratan sulfate in an unknown specimen may be quantitated, and this invention is not limited to any particular form that an immunoassay may take. Enzyme-linked or other nonradioactive colorimetric assay procedures are preferred to radioimmunoassay techniques from the standpoint of safety considerations and reagent stability.

The development of an assay sensitive to levels of keratan sulfate in peripheral fluids was made possible in part through the development of monoclonal antibodies specifically reactive with keratan sulfate. The first of these was developed by Bruce Caterson, *J. of Biological Chemistry* 258, 8848–8854 (1983) when developing monoclonal antibodies against cartilage tissue. It was found that certain of these monoclonal antibodies are specifically reactive with the keratan sulfate moiety and are reactive therewith when the keratan sulfate moiety exists as a separate entity. Since then, other keratan sulfate-specific monoclonal antibodies have been developed.

Because of the substantial similarities of keratan sulfates of mammalian species, monoclonal antibodies reactive with keratan sulfate from one species are often reactive with keratan sulfate from another species. However, reactivity of the antibodies with keratan sulfate may differ from one species to another, and if keratan sulfate standards are obtained from a species that is different from the species in which keratan sulfate level is being measured, the keratan sulfate level may be expressed in equivalents of the standard. Alternatively, the levels may be correlated by a conversion factor that is derived by independent measurements. One of the most standardized keratan sulfate-containing material is bovine nasal D1 proteoglycan (BNP), against which human blood keratan sulfate levels may be measured, in which case human blood levels may be expressed as ng/ml, BNP equivalents. To convert to human keratan sulfate concentrations, BNP equivalents are multiplied by a factor of 0.10.

It is also known that the reactivity of the monoclonal antibody, such as has been developed by Bruce Caterson, with keratan sulfate is dependent somewhat upon the degree of sulfation, giving rise to some degree of uncertainty of absolute keratan sulfate level in an immunoassay. Nevertheless, the ELISA is sufficiently quantitative to detect clearly abnormal levels of keratan sulfate. The ELISA has good reproducibility on the same sample, even when performed by different technicians. Furthermore, it is found that the peripheral blood level of keratan sulfate in a particular patient, at any one time during a twenty-four hour period, tends to remain quite steady. Thus, any significant change in a patient's keratan sulfate level may represent either a deterioration of his condition or a response to treatment.

It is found that normal adult peripheral human blood serum or plasma contains between approximately 3000 and approximately 9000 ng/ml, BNP equivalents, which corresponds to between approximately 300 and approximately 900 ng/ml of human keratan sulfate. Keratan sulfate levels above approximately 900 ng/ml are considered abnormally high in an adult human and may be indicative of cartilage-group tissue deterioration, e.g., osteoarthritis. Keratan sulfate levels below 300 ng/ml in an adult are considered abnormally low and may be indicative of keratan sulfate defficiency. Keratan sulfate levels above 1100 ng/ml or below 100 ng/ml in an adult human are considered strongly indicative of abnormal cartilage metabolism. It is to be understood that these levels are expressed numerically in terms of a specific standard, and that with other standards, these reference numbers may vary. More generally, keratan sulfate levels more than about 10% above the mean and particularly more than about 30% above the mean are considered abnormally high and levels below about 40% of the mean and particularly below about 20% of the mean are considered abnormally low. It should also be noted that normal keratan sulfate levels in adult humans are somewhat age dependent and that more precise diagnoses will be available when normal keratan sulfate levels are more closely correlated with age groups. Children generally have higher keratan sulfate levels than do adults, and normal values will have to be worked out for children at various stages of development.

Although it is clearly demonstrated that osteoarthritis patients tend to have abnormally high levels of keratan sulfate whereas patients suffering from macular dystrophy have been found to have either substantially no keratan sulfate or quite elevated levels of keratan sulfate in their peripheral blood, there is some overlap of the level ranges between patients presumed to have normal cartilage-group tissue and those with an abnormal expression of or deterioration of cartilage-group tissue. Thus abnormal keratan sulfate levels are indicative, but not always conclusive, of cartilage-group tissue abnormalities, and normal levels of keratan sulfate do not rule out cartilage-group tissue abnormalities. Nevertheless, at certain abnormal levels, the probabilities increase significantly that an individual has a cartilage group tissue abnormality.

The invention will now be described in greater detail by way of specific examples.

EXAMPLE 1

Nine polystyrene plates are placed in 50% ethanol for 30 minutes. The plates are then air dried, and 200 microliters of a 20 mM carbonate/bicarbonate, 0.02% sodium azide, pH 9.2, buffer solution containing BNP is placed in each of the 96 wells. Each plate is placed in a plastic bag and stored at 4° C. for use within 90 days.

The assay itself is performed as follows. 150 μl of unknown blood serum specimens and 150 μl of BNP standards ranging in concentration from 5 to 0.04 ug/ml are incubated for one hour with 150 μl of anti-keratan sulfate 1/20/5-D-4 antibody, Caterson, supra., at 1/2000 in 1% BSA, phosphate buffered saline, 0.05% Tween 20, containing 5 mM EDTA.

At the end of the one hour period, 200 μl of the incubation mixture is placed in a well of a prepared plate for 1 hour at 37° C. This is followed by washes (3×5 minutes) with phosphate buffered saline, Tween 0.05%, following which the wells are drained of liquid and 200 μl of anti-mouse IgG coupled to peroxidase (in 1% BSA, phosphate buffered saline, Tween 20, 0.05%) is added to each well. After one hour, the solutions are removed and the wells are rinsed (3×5 minutes).

A solution of substrate (*Journal of Biological Chemistry*, (1982) *supra.*) for reporting the presence of peroxidase is then added and the color is allowed to develop for 60 minutes. The amount of color produced in each case is determined as described, using a Titertek multiscan instrument (Flow Laboratories). The $Å_{492}$ values obtained at the end of the assay are compared with a standard curve constructed from $Å_{492}$ values obtained for known amounts of purified BNP.

EXAMPLE 2

In a blind study, 40 serum samples were submitted for assay without patient names or case histories provided. After performance of the assays, it was revealed that six of the samples were obtained from a patient (designated patient 1) diagnosed as having macular dystrophy and three of the samples were from a second patient (designated patient 2) diagnosed as having a corneal disorder related to macular dystrophy. The results are tabulated in Table 1 below.

TABLE 1

| | Keratan Sulfate ng/ml |
|---|---|
| Macular Dystrophy | <54, <54, <54, <54, <54, <54. PATIENT 1 (repeat specimens) |
| Corneal Disorder | 1992, 2085, 2234. PATIENT 2 (repeat specimens) |
| Absence of Macular Dystrophy (Relative of the two patients with Macular Dystrophy) | N = 31 Mean = 980 ± 198 642, 662, 674, 691, 739, 795, 811, 835, 850, 868, 888, 910, 920, 944, 954, 997, 999, 1009, 1033, 1075, 1081, 1093, 1109, 1120, 1125, 1132, 1256, 1256, 1276, 1302, 1346 |

Patient 1 had essentially no keratan sulfate in his blood serum. Patient 2 had highly elevated levels of keratan sulfate in his blood serum. Thus abnormal levels of keratan sulfate in the blood appears to be indicative of macular dystrophy and related disorders. The repeat samples further indicate good reproducibility of results of the assay.

EXAMPLE 3

180 blood serum specimens were obtained from a general hospital population, exclusive of patients being treated for joint diseases. (This does not represent a general population and does not exclude patients who may have joint diseases but were in the hospital for other reasons.) 117 blood specimens were also obtained from patients in the same hospital that were under treatment for joint diseases. All blood samples were assayed for keratan sulfate according to the method of Example 1.

After the results were determined, the case histories of the patients with joint disease were reviewed, and the results were recalculated for all of the 117 joint diseases patients who were previously diagnosed as having osteoarthritis. The results are summarized in Table 2 below.

TABLE 2

Content of Keratan Sulfate in Adult Human Sera

| | Number of Patients | Keratan Sulfate ng/ml Mean, S.D. | % of Patients having Keratan Sulfate Levels above 900 ng/ml |
|---|---|---|---|
| General Hospital Population | 180 | 832 ± 397 | 34.4 |
| Patients With Joint Diseases | 117 | 986 ± 268 | 57.3 |
| Patients With Osteoarthritis | 11 | 1195 ± 286 | 81.8 |

It can be seen that although the keratan sulfate levels in the blood samples of the general and symptomatic groups overlap, a patient having a keratan sulfate level above about 900 ng/ml in his peripheral serum blood is much more likely to be in the joint disease population than in the general population. In the group known to have osteoarthritis the results are more dramatic, with elevated levels of keratan sulfate providing a substantial indication of cartilage deterioration.

From the above table, it is concluded that a keratan sulfate level of 900 ng/ml or above is indicative of cartilage-group tissue deterioration and that patients having elevated levels of keratan sulfate, particularly older patients, might be examined further for other indications of cartilage tissue deterioration. Although it is true that approximately a third of the general hospital population had keratan sulfate levels above the selected threshold level of 900 ng/ml, it must be remembered that this is not really a general population, but rather contains a disproportionately high percentage of older patients, many of whom might be expected to have osteoarthritis.

While the invention has been described in terms of certain preferred embodiments, modifications obvious to one with ordinary skill in the art may be made without departing from the scope of the invention. For example, there is not any requirement that the antibody used in the immunoassay be monoclonal, and a polyclonal antibody fraction may be used, providing that it is sufficiently specific for keratan sulfate. However, in view of the fact that monoclonal antibodies are available, use of monoclonal antibody is certainly preferred. The invention has been described primarily in terms of measuring keratan sulfate levels in the peripheral blood of humans where diagnosis of cartilage group tissue abnormalities is of most interest; however, the method is applicable to lower animals as well, and because of the preservation of the structure of keratan sulfate in a variety of mammalian species, the assay as described herein may in many cases be used employing the same monoclonal antibodies for diagnosing abnormal levels of keratan sulfate in lower mammals.

Various features of the invention are set forth in the following claims.

What is claimed:

1. A method for indicating an abnormality of cartilage, disc or corneal tissue in a mammal, which method comprises measuring, by an immunoassay of a specimen of the peripheral blood serum or plasma of the mammal employing a monoclonal antibody reactive with keratan sulfate, the level of keratan sulfate in said specimen and noting an abnormal level of keratan sulfate in said specimen.

2. A method according to claim 1 wherein the mammal is human.

3. A method according to claim 2 wherein the abnormality to be indicated is osteoarthritis and the level of keratan sulfate in the specimen of serum or plasma is abnormally high.

4. A method according to claim 2 wherein the abnormality to be indicated is mascular corneal dystrophy and the level of keratan sulfate in the specimen of serum or plasma is abnormally low.

5. A method according to claim 3 wherein the immunoassay is an enzyme-linked immunosorbent assay.

6. A method according to claim 4 wherein the immunoassay is an enzyme-linked immunosorbent assay.

* * * * *

UNITED STATES PATENT AND TRADEMARK OFFICE
CERTIFICATE OF CORRECTION

PATENT NO. : 4,704,356
DATED : November 3, 1987
INVENTOR(S) : Eugene J. Thonar

It is certified that error appears in the above-identified patent and that said Letters Patent is hereby corrected as shown below:

In the abstract, Line 8:  Change "muscular" to --macular--.
Column 8, Line 54:  Change "mascular" to --macular--.

Signed and Sealed this

Seventh Day of June, 1988

Attest:

Attesting Officer

DONALD J. QUIGG

Commissioner of Patents and Trademarks